United States Patent [19]

Lösel et al.

[11] Patent Number: 5,707,638

[45] Date of Patent: Jan. 13, 1998

[54] INSECTICIDAL ATTRACT-AND-KILL FORMULATIONS

[75] Inventors: Peter Lösel, Monheim; Gunther Penners, Leverkusen; Joachim Weissmüller, Monheim, all of Germany

[73] Assignee: Bayer Aktiengesellschaft, Leverkusen, Germany

[21] Appl. No.: 575,254

[22] Filed: Dec. 20, 1995

[30] Foreign Application Priority Data

Dec. 23, 1994 [DE] Germany ............... 44 46 344.8

[51] Int. Cl.[6] ..................................... A01N 25/24
[52] U.S. Cl. ..................... 424/407; 424/405; 424/409
[58] Field of Search ........................ 424/405–407, 424/409–417, 419, 84

[56] References Cited

U.S. PATENT DOCUMENTS

| | | | |
|---|---|---|---|
| 3,127,235 | 3/1964 | Benzel | 424/406 |
| 4,456,587 | 6/1984 | Keith | 424/78 |
| 4,666,747 | 5/1987 | Quinn | 427/421 |

FOREIGN PATENT DOCUMENTS

| | | |
|---|---|---|
| 0257415 | 3/1988 | European Pat. Off. |
| 999067 | 7/1965 | United Kingdom . |
| 2018593 | 10/1979 | United Kingdom . |
| 2138291 | 10/1984 | United Kingdom . |

*Primary Examiner*—Neil S. Levy
*Attorney, Agent, or Firm*—Sprung Kramer Schaefer & Briscoe

[57] ABSTRACT

New pesticidal compositions which dry and harden after application, said compositions consisting of
- at least one pesticidally active compound,
- at least one signal substance,
- at least one liquid UV absorber which is only sparingly miscible with water,
- at least one curable polymer which, after drying of the formulation, has a sponge-like structure or forms a porous film
- at least one surfactant and,
- if appropriate, additives.

The new compositions are very suitable for combating insects and undesirable representatives of the order Acarina.

2 Claims, No Drawings

INSECTICIDAL ATTRACT-AND-KILL FORMULATIONS

The present invention relates to novel compositions for combating harmful insects and representatives of the order Acarina, to a process for the preparation of these compositions, and to their use in agriculture, forestry and in horticulture.

When combating animal pests of plants with the aid of pesticides, an effort is made to minimize contamination of the plants to be protected and of their environment including the soil on which they grow. Moreover, beneficial animals and warm-blooded species are to be adversely affected as little as possible by the pesticidally active compounds. In contrast, however, the pests to be combated are to be exposed as much as possible to the pesticidally active compounds, so that the pests can take up the active compounds in a sufficient amount by means of contact, as stomach poisons or via the gas phase.

When combating insects, the abovementioned conditions can be met for example by combining insecticidally active compounds with signal substances, such as pheromones, kairomones or attractants, which have an attractant action on insects, and applying the resulting mixtures to the crop to be protected not over the entire area, but only locally to small individual spots. Since the signal substances are also released at the treated sites, the pests migrate to these sites, become contaminated with the pesticidally active compounds and are destroyed.

To allow such compositions to be active over a sufficiently long period, the active components must be present in the formulations in question in such a form that, on the one hand, they are protected against environmental factors, such as light, oxygen and climate, but, on the other hand, they are also released in a controlled manner. Moreover, it must be guaranteed that the insects take up such an amount of active compound after coming into contact with the formulation as is sufficient to destroy them.

A large number of preparations based on the above-described concept for controlling animal pests has already been disclosed.

EP-A 0 055 475, for example, discloses that male insects of the species Cossus cossus can be combated with the aid of (Z)-5-dodecen-1-yl acetate, if appropriate in the form of a mixture with (Z)-3-decen-1-yl acetate, (Z)-3-dodecen-1-yl acetate and/or (E)-5-dodecen-1-yl acetate. The attractant, or mixtures of the active components, are applied in solvents which have a low vapour pressure or alternatively, if desired, in the form of an adsorbate on inert solids as a mixture with antioxidants and UV stabilizers. Moreover, GB-A 2 064 323 describes pheromone-based insecticides in which the signal substances and UV stabilizers and other additives are fixed to a combination of absorbing and adsorbing solids. However, the disadvantage of these preparations is that their resistance to climatic factors is only relatively low and that the active compounds are broken down or leached out after only a relatively short time.

For combating pests, it is furthermore already known to employ combinations of attractants and insecticides in microencapsulated form or bound in water-soluble polymers (of. JP-A 59-7101 and "Advances in Pesticide Formulation Technology" 1984., Chapter 11, pages 151–162). However, the action of such formulations is not always sufficiently high since the amount of active compound released is frequently inadequate for destroying the pests.

In accordance with GB-A 2 141 932, preparations which comprise pheromones, if appropriate as a mixture with UV absorbers and other additives, in liquid or semi-liquid, water-resistant and UV-stabilizing polymers can be used as pesticides. While the active components remain stable over a sufficiently long period in these formulations, the amount of active compound which diffuses out does not always guarantee a sufficiently high degree of action. Moreover, the use of such compositions, which retain their liquid consistency even after application, sometimes causes problems in practice.

Finally, it can be seen from EP-A 0 376 888 that other formulations which are suitable for combating pests are those which are mainly composed of one or more permanently liquid UV absorbers, as well as insecticides and attractants, and which are in viscous form and do not harden, even over a prolonged period. The activity of these preparations is good, but their use in practice causes problems. If, for example, the treated area under cultivation regularly requires further manual working, as is the case with fruit crops grown as trees and in viticulture, it will hardly be possible in the treated crops to avoid contamination of the user with active compound. Moreover, environmental factors can cause undesirable wide distribution of the permanently liquid preparations over the entire area under cultivation.

There have now been found new pesticidal compositions which comprise

- at least one pesticidally active compound,
- at least one signal substance,
- at least one liquid UV absorber which is only sparingly miscible with water,
- at least one curable polymer which, after drying of the formulation, has a sponge-like structure or forms a porous film
- at least one surfactant and
- if appropriate additives and which dry and harden after application.

Furthermore, it has been found that compositions according to the invention can be prepared by a) mixing at least one pesticidally active compound, at least one signal substance, at least one liquid UV absorber which is only sparingly miscible with water and, if appropriate, additives, b) dispersing the resulting mixture in a solution of at least one surfactant and water and c) treating the resulting emulsion with an aqueous solution or dispersion of at least one curable polymer which, after drying of the formulation, has a sponge-like structure or forms a porous film, and, if appropriate, with additives.

Finally, it has been found that the compositions according to the invention are highly suitable for combating harmful insects and undesirable representatives of the order Acarina in agriculture, forestry and in horticulture.

It is extremely surprising that the compositions according to the invention which harden after application are highly suitable for the abovementioned purpose. This is because the above-described prior art suggested that the pests to be combated do not take up an mount of active compound of such preparations which solidify after application which suffices to destroy them. However, in contrast to expectations, the compositions according to the invention have a better, or at least equally good, activity as prior-art formulations of similar composition which remain viscous after application.

The compositions according to the invention are distinguished by a series of advantages. For example, these preparations are highly stable, even under unfavourable climatic conditions. Furthermore, they allow targeted, highly efficient, environmentally friendly pest control over a prolonged period. Since the compositions according to the invention solidify after application, there is, moreover, virtually no danger of persons who work in the treated crops becoming contaminated with pesticidally active compounds. Finally, the curable compositions adhere to the sites to which they have been applied. Environmental factors do not cause undesirable wide distribution.

The compositions according to the invention comprise one or more pesticidally active compounds. These are to be understood as meaning all customary substances which are suitable for combating harmful insects and undesirable representatives of the order Acarina. The following are preferably suitable, carbamates, organophosphorus compounds, nitrophenols and their derivatives, nitromethylenes, nicotinoids, formamidines, ureas, phenylbenzoylureas, pyrethroids, chlorinated hydrocarbons and Bazillus thuringensis preparations. The following substances may be mentioned as examples:

abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, betacyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184699, chloethocarb, chlorethoxyfos, chlorfenvinphos, chlorfluazuron, chlormephos, chlorpyrifos, chlorpyrifos M, cis-Resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram omethoat, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos,

RH 5992, salithion, sebufos, silafluofen, sulfotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, transfluthrin vamidothion, XMC, xylylcarb, zetamethrin.

Signal materials which the compositions according to the invention comprise can be all customary substances which have an attractant action on the pests to be combated and which alter the behaviour of these pests. Signal substances which are preferably suitable are pheromones, kairomones and attractants. Examples of such materials which may be mentioned are the following substances:

Z-5-decenyl acetate, dodecanyl acetate, Z-7-dodecenyl acetate, E-7-dodecenyl acetate, Z-8-dodecenyl acetate, E-8-dodecenyl acetate, Z-9-dodecenyl acetate, E-9-dodecenylacetate, E-10-dodecenyl acetate, 11-dodecenyl acetate, Z-9, 11-dodecadienyl acetate, E-9, 11-dodecadienyl acetate, Z-11-tridecenyl acetate, E-1-tridecenyl acetate, tetradecenyl acetate, E-7-tetradecenyl acetate, Z-8-tetradecenyl acetate, E-8-tetradecenyl acetate, Z-9-tetradecenyl acetate, E-9-tetradecenyl acetate, Z-10-tetradecenyl acetate, E-10-tetradecenyl acetate, Z-11-tetradecenyl acetate, E-11-tetradecenyl acetate, Z-12-pentadecenyl acetate, E-12-pentadecenyl acetate, hexadecanyl acetate, Z-7-hexadecenyl acetate, Z-11-hexadecenyl acetate, E-11-hexadecenyl acetate, octadecanyl acetate, E,Z-7,9-dodecadienyl acetate, Z,E-7,9-dodecadienyl acetate, E,E-7,9-dodecadienyl acetate, Z,Z-7,9-dodecadienyl acetate, E,E-8,10-dodecadienyl acetate, E,Z-9,12-dodecadienyl acetate, E,Z-4,7-tridecadienyl acetate, 4-methoxy-cinnamaldehyde, β-ionone, estragole, eugenol, indole, 8-methyl-2-decyl propanoate, E,E-9, 11-tetradecadienyl acetate, Z,Z-9,12-tetradecadienyl acetate, Z,Z-7,11 -hexadecadienyl acetate, E,Z-7,11-hexadecadienyl acetate, Z,E-7,11-hexadecadienyl acetate, E,E-7,11-hexadecadienyl acetate, Z,E-3,13-octadecadienyl acetate, E,Z-3,13-octadecadienyl acetate, E,E-3,13-octadecadienyl acetate, ethanol, hexanol, heptanol, octanol, decanol, Z-6-nonenol, E-6-nonenol, dodecanol, 11-dodecenol, Z- 7-dodecenol, E-7-dodecenol, Z-8-dodecenol, E-8-dodecenol, E-9-dodecenol, Z-9-dodecenol, E-9,11-dodecadienol, Z-9, 11-dodecadienol, Z,E-5,7-dodecadienol, E,E-5,7-dodecadienol, E,E-8,10-dodecadienol, E,Z-8,10-dodecadienol, Z,Z-8,10-dodecadienol, Z,E-8,10-dodecadienol, E,Z-7,9-dodecadienol, Z,Z-7,9-dodecadienol, E-5-tetradecenol, Z-8-tetradecenol, Z-9-tetradecenol, E-9-tetradecenol, Z-10-tetradecenol, Z-11-tetradecenol, E-11-tetradecenol, Z-11-hexadecenol, Z,E-9,11-tetradecadienol, Z,E-9,12-tetradecadienol, Z,Z-9,12-tetradecadienol, Z,Z- 10, 12-tetradecadienol, Z,Z-7,11-hexadecadienol, Z,E-7, 11-hexadecadienol, (E)-14-methyl-8-hexadecen-1-ol, (Z)-14-methyl-8-hexadecen-1-ol, E,E-10,12-hexadecadienol, E,Z-10,12-hexadecadienol, dodecanal, Z-9-dodecenal, tetradecanal, Z-7-tetradecenal, Z-9-tetradecenal, Z-11-tetradecenal, E-11-tetradecenal, E-11,13-tetradecadienal, E,E-8,10-tetradecadienal, Z,E-9,11 -tetradecadienal, Z,E-9, 12-tetradecadienal, hexadecanal, Z-8-hexadecenal, Z-9-hexadecenal, Z-10-hexadecenal, E-10-hexadecenal, Z-11-hexadecenal, E-11-hexadecenal, Z-12-hexadecenal, Z-13-hexadecenal, (Z)- 14-methyl-8-hexadecenal, (E)- 14-methyl-8-hexadecenal, Z,Z-7, 11-hexadecadienal, Z,E-7,11-hexadecadienal, Z,E-9, 11-hexadecadienal, E,E-10,12-hexadecadienal, E,Z-10, 12-hexadecadienal, Z,E-10,12-hexadecadienal, Z,Z-10, 12-hexadecadienal, Z,Z-11,13-hexadecadienal, octadecanal, Z-11-octadecenal, E-13-octadecenal, Z-13-octadecenal, Z-5-decenyl-3-methyl- butanoate Disparlure: (+) cis-7,8-epoxy-2-methyloctadecane, Seudenol: 3-methyl-2-cyclohexen-1-ol, sulcatol: -methyl-5-hepten-2-ol, Ipsenol: 2-methyl-6-methylene-7-octen-4-ol, Ipsdienol: 2-methyl-6-methylene-2,7-octadien-4-ol, Grandlure I: cis-2-isopropenyl-1-methyl-cyclobutanethanol, Grandlure II: Z-3,3-dimethyl-1-cyclohexanethanol, Grandlure III: Z-3,3-dimethyl-1-cyclohexaneacetaldehyde, Grandlure IV: E-3,3-dimethyl-1-cyclohexaneacetaldehyde, cis-2-verbenol: cis-4,6,6-trimethylbicyclo[3,1,1 ]hept-3-en-2-ol cucurbitacin, 2-methyl-3-buten-2-ol, 4-methyl-3-heptanol, cucurbitacin, 2-methyl-3-buten-2-ol, 4-methyl-3-heptanol, α-pinene: 2,6,6-trimethylbicyclo [3,1,1]hept-2-ene, α-caryophyllene: 4,11,11-trimethyl-8-methylenebicyclo[7,2,0]undecane, Z-9-tricosene, α-multistriatin 2(2-endo, 4-endo)-5-ethyl-2,4-dimethyl-6,8-dioxabicyclo[3,2, 1 ]octane, methyleugenol: 1,2-dimethoxy-4-(2-propenyl)phenol, Lineatin: 3,3,7-trimethyl-2,9-dioxatricyclo[3,3,1,0]nonane, Chalcogran: 2-ethyl-1,6-dioxaspiro[4,4]nonane, Frontalin: 1,5-Dimethyl-6,8-dioxabicyclo[3,2, 1 ]octane, endo-Brevicomin: endo-7-ethyl-5-methyl-6,8-dioxabicyclo[3,2, 1 ]octan, exo-brevicomin: exo-7-ethyl-5-methyl-6,8-dioxabicyclo[3,2, 1 ]octane, (Z)-5-(1-decenyl)dihydro-2-(3H)-furanone, Farnesol 3,7-11-trimethyl-2,6,10-dodecatrien-1-ol, Nerolidol 3,7-,11-trimethyl-1,6,10-dodecatrien-3-ol, 3-m ethyl ,6-(1-methyl ethenyl)-9-decen-1-ol acetate, (Z)-3-methyl-6-(1-methylethenyl)-3,9-decadien-1-ol acetate, (E)-3,9-methyl-6-(1-methylethenyl)-5,8-decadien-1-ol-acetate, 3-methylene-7-methyl-octen-1-ol propionate, (Z)-3,7-dimethyl-2,7-octadien-1-ol propionate, (Z)-3, 9-dimethyl-6-(1-methylethenyl)-3,9-decadien-1-ol propionate.

The compositions according to the invention comprise at least one liquid UV absorber which is only sparingly miscible with water. This is to be understood as meaning substances which are capable of absorbing UV light, preferably UV radiation from the sunlight in a wavelength range of from 270 to 400 nm. Liquid UV absorbers which are preferably suitable are

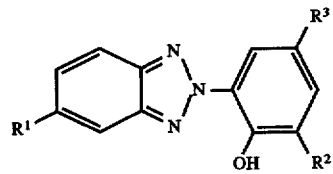

(I)

in which

R¹ represents hydrogen or chlorine,

R² represents hydrogen, alkyl, phenylalkyl or phenyl and

R³ represents alkyl, phenylalkyl, phenyl or —(CH₂)₂—COO—alkyl, 2-hydroxy-4-alkoxy-benzophenones of the formula

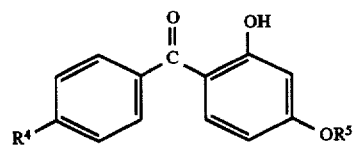

(II)

in which

R⁴ represents hydrogen, alkyl or alkoxy and

R⁵ represents alkyl, preferably methyl, isooctyl or dodecyl, oxalanilides of the formula

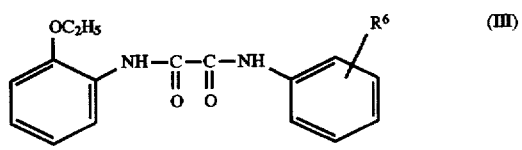

(III)

in which

R⁷ represents alkyl, cinnamic acid derivatives of the formulae

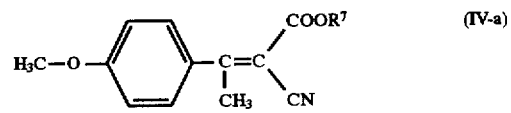

(IV-a)

in which

R⁷ represents alkyl, preferably n-butyl, or

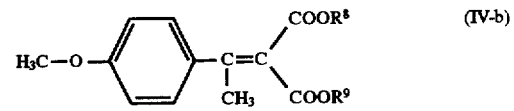

(IV-b)

in which

R⁸ and R⁹ represent alkyl, or

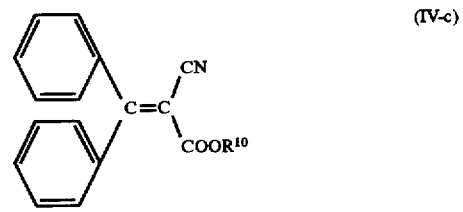

(IV-c)

in which

R¹⁰ represents alkyl, preferably butyl or the radical

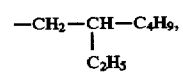

and triazine derivatives of the formula

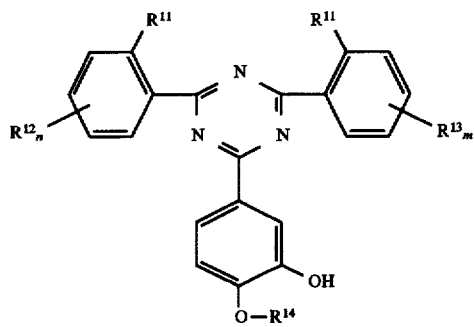

(V)

in which

R$^{11}$ represents hydrogen or hydroxyl,

R$^{12}$ represents alkyl having 1 to 18 carbon atoms,

R$^{13}$ represents alkyl having 1 to 18 carbon atoms or alkoxy having 1 to 18 carbon atoms, R$^{14}$ represents alkyl having 1 to 18 carbon atoms and m and n represent the numbers 0, 1 or 2.

Examples of 2-(2-hydroxyphenyl)-benzotriazoles of the formula (I) which may be mentioned are the materials listed in Table 1 below:

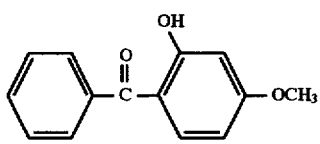

(II-1)

may be mentioned.

As an example of a cinnamic acid derivative of the formula (IV-c), 2-(2-ethylhexyl) 2-cyano-3,3-diphenyl-2-propenoate, of the formula

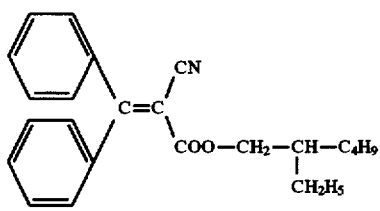

(IV-1)

may be mentioned.

Suitable polymers which the compositions according to the invention comprise are all customary water-soluble or water-dispersible polymers or copolymers which, after application of the compositions, dry as a film to form a sponge-like, porous matrix. Polymers which are preferably

TABLE 1

| Trade name | R$^1$ | R$^2$ | R$^3$ |
|---|---|---|---|
| Tinuvin 109 (I-1) | Cl | —C(CH$_3$)$_3$ | 50% —CH$_2$—CH$_2$—C(=O)—O—C$_8$H$_{17}$ <br><br> 50% —CH$_2$—CH$_2$—C(=O)—O—CH(C$_2$H$_5$)—C$_4$H$_9$ |
| Tinuvin 171 (I-2) | H | —C$_{12}$H$_{25}$— (Isomer mixture) | —CH$_3$ or C$_2$—C$_{12}$-alkyl |
| Tinuvin 1130 (I-3) | H | —C(CH$_3$)$_3$ | approx. 50% —CH$_2$—CH$_2$—C(=O)—O—(CH$_2$—CH$_2$—O)$_{300}$—H <br><br> approx. 38% —[CH$_2$—CH$_2$—C(=O)—O—(CH$_2$—CH$_2$—O)$_{150}$—]$_2$ <br><br> approx. 12% polyethylene glycol (EO 300) |
| "SL 874" (I-4) | H | —C(CH$_3$)$_3$ | —CH$_2$—CH$_2$—C(=O)—O—(CH$_2$)$_8$—CH=CH—(CH$_2$)$_7$—CH$_3$ |

As an example of a compound of the formula (II) 2-hydroxy-4-methoxybenzophenone, of the formula suitable are those which can be synthesized by means of anionic or non-ionic polymerization of suitable monomers, for example by emulsion polymerization or bead polymerization with the aid of free-radical initiators or other initiator systems. Other polymers which can preferably be employed are those based on natural rubber latices.

Examples of particularly preferred polymers which may be mentioned are the following substances: polyvinyl acetate (Mowilith®), polyvinyl alcohols with various degrees of hydrolyzation (Mowiol®), polyvinylpyrrolidones (Luviskol K®, Agrimer®), polyacrylates (Carbopol®), acrylate-, polyol- or polyester-based varnish-system binders which are soluble or dispersible in water (Desmophen®, Roskydal®, Bayhydrol®), furthermore copolymers of two or more monomers such as acrylic acid, methacrylic acid, itaconic acid, maleic acid, fumaric acid, maleic anhydride, vinylpyrrolidone, ethylenically unsaturated monomers such as ethylene, butadiene, isoprene, chloroprene, styrene, divinylbenzene, α-methylstyrene or p-methyl-styrene, furthermore vinyl halides, such as vinyl chloride and vinylidene chloride, moreover vinyl esters, such as vinyl acetate, vinyl propionate or vinyl stearate, and also vinyl methyl ketone, or esters of acrylic acid or methacrylic acid with monohydric alcohols or polyols, such as methyl acrylate, methyl methacrylate, ethyl acrylate, ethylene methacrylate, lauryl acrylate, lauryl methacrylate, decyl acrylate, N,N-dimethylamino ethyl methacrylate, 2-hydroxyethyl methacrylate, 2-hydroxypropyl methacrylate or glycidyl methacrylate, furthermore diethyl esters or monoesters of unsaturated dicarboxylic acids, or else (meth) acrylamido-N-methylol methyl ether, amides or nitriles, such as acrylamide, methacrylamide, N-methylol-(meth) acrylamide, acrylonitrile, methacrylonitrile, and also N-substituted maleinimides and ethers, such as vinyl butyl ether, vinyl isobutyl ether or vinyl phenyl ether.

When the formulations dry, the polymersform a matrix which is not or only sparingly soluble, or sparingly dispensible, in water. Polymers which have a low glass transition temperature are preferably employed, in particular those substances with a glass transition temperature of below 50° C.

The compositions according to the invention comprise one or more surfactants. Suitable surface-active substances are all those which are conventionally used in the production of plant treatment products. The following are preferably suitable: non-ionic and anionic emulsifiers, such as polyoxyethylene fatty acid esters, polyoxyethylene fatty alcohol ethers, alkylaryl polyglycol ethers, fatty amine ethoxylates, alkylsulphonates, alkyl sulphates, alkylarylsulphonates, aryl sulphates and silicone surfactants. Examples of such surface-active substances are listed in McCutcheon's "Emulsifiers and Detergents" 1982 North America Edit., MC Publishing Co., 175 Rock Road, Glen Rock, N.J. 07 452, USA.

Suitable additives which may be present in the compositions according to the invention are all those which can conventionally be used as additives in plant treatment products. These include colourants, antioxidants, thickeners, fillers, antifreeze agents and solvents.

Suitable colorants are soluble dyes or sparingly soluble colour pigments, such as, for example, titanium dioxide, pigment-grade colour black or zinc oxide.

Suitable antioxidants are all substances which can conventionally be employed for this purpose in plant treatment products. Sterically hindered phenols and alkyl-substituted hydroxyanisoles and hydroxytoluenes are preferred.

Thickeners which are suitable are all substances which can conventionally be employed for this purpose in plant treatment products. The following are preferably suitable: organic polymers, such as partially or fully neutralized polyacrylic acids (Carbopol®), polyethylene glycols (Polyox®), polyvinyl alcohols and non-ionically or ionically modified celluloses (Tylose®), xanthan-based thixotropic thickeners (Kelzan®), and also inorganic disperse thickeners, such as precipitated or pyrogenic silicas, kaolins, bentonites and aluminium/silicon mixed oxides.

Suitable antifreeze agents are all substances which can conventionally be employed for this purpose in plant treatment products. Urea, glycerol or propylene glycol are all preferably suitable.

Fillers are, again, all inert materials which can conventionally be employed for this purpose in plant treatment products. The following are preferably suitable: rockmeals, calcium carbonate, quartzmeal and aluminum/silicon mixed oxides or mixed hydroxides.

Solvents which are suitable are all inert organic solvents which can conventionally be employed for this purpose in plant treatment products. The following are preferred: glycols, such as propylene glycol and polyethylene glycols of different molecular weight ketones, such as methyl isobutyl ketone, methyl isopropyl ketone and cyclohexanone; amides, such as dimethylformamide or diethylformamide; N,N-dialkylated carboxamides (for example Hallcomid®); alkyl lactams, such as substituted pyrrolidones (for example N-methylpyrrolidone and Surfadone®) and caprolactams (for example Azone®); hydrocarbons, n-paraffins and iso-paraffins having different boiling ranges as they are obtainable, for example, under the commercial names Exxol®, Norpar® and Isopar®; aromatic hydrocarbons, such as xylene and aromatic distillation fractions (for example Solvesso®); esters, such as propylene glycol monomethyl ether acetate, dibutyl adipate and di-n-butyl phthalate; ethers, such as propylene glycol methyl ether or propylene glycol butyl ether; alcohols, such as ethanol, n- and i-propanol, n- and i-butanol, n- and i-amyl alcohol, benzyl alcohol, tetrahydrofurfuryl alcohol, 1-methoxy-2-propanol, and higher alcohols, and furthermore dimethyl sulphoxide, dioxane and tetrahydrofuran. The solvents can be employed in the form of individual components or of mixtures. Particularly preferred are those which are miscible with the UV stabilizer and which are not unduly volatile.

The concentrations of individual components in the compositions according to the invention can be varied within a substantial range. After deducting the water present in the compositions according to the invention, the concentrations of pesticidally active compounds are generally between 0.1 and 10% by weight, preferably between 1 and 4% by weight, of signal substances are generally between 0.01 and 1% by weight, preferably 0.05 and 0.3% by weight, of UV absorbers are generally between 10 and 80% by weight, preferably between 40 and 70% by weight, of polymers of generally between 10 and 90% by weight, preferably between 25 and 75% by weight, of surface-active substances of generally between 0.1 and 4% by weight, preferably between 0.2 and 2% by weight, and of additives are generally between 0 and 50% by weight, preferably between 0 and 25% by weight.

In addition, the compositions according to the invention also comprise water. The water content prior to drying varies within a substantial range. It is generally between 50 and 90% by weight.

When preparing the compositions according to the invention, a procedure is generally followed in which a premix is first prepared by dissolving or dispersing at least one pesticidally active compound and at least one signal substance in at least one liquid UV absorber with stirring at temperatures between 20° C. and 50° C., preferably at room temperature, and, if appropriate, additives are added. The premix is then dispersed into a stirred solution of at least one surfactant in water at temperatures between 20° C. and 50°

C., preferably at room temperature. The dispersing process is carried out in such a way that an oil-in-water emulsion is formed in which the mean particle size is generally between 0.5 and 50 μm, preferably between 1 and 20 μm. The resulting emulsion is subsequently treated with a solution or dispersion of at least one polymer in water and, if appropriate, additives, at temperatures between 20° C. and 50° C., preferably at room temperature, with stirring. However, a different procedure may be followed when preparing the compositions according to the invention. In principle, it is possible to mix the components in any desired sequence. All stirring and mixing apparatus customary for the preparation of the compositions according to the invention is suitable.

Upon preparation, the compositions according to the invention are obtained in a liquid or viscous state. After application, the viscous compositions dry and form a non-flowable, non-tacky coating with good adhesive properties which has a sponge-like structure or forms a porous film. Once dry, the coating has a firm to rubber-like consistency.

The compositions according to the invention are highly suitable for combating harmful insects and undesirable representatives of the order Acarina, which are encountered in agriculture, in forestry and in horticulture including viticulture. They can be used against the pests mentioned below.

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides,* Melanoplus differentialis and *Schistocerca gregaria.*

From the order of the Dermaptera, for example, *Forficula auricularia.*

From the order of the Isoptera, for example, Reticulitermes spp..

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Bruchidius obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp..

From the order of the Arachnida, for example, *Scorpio maurus* and *Latrodectus mactans.*

From the order of the Acarina, for example, Acarus siro, Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonerous spp., *Bryobia praetiosa,* Panonychus spp. and Tetranychus spp..

The compositions according to the invention can be applied to the plants or areas under cultivation to be treated in the form of droplets, drop-like areas or thin defined layers by using conventional devices as they are known to those skilled in the art. Particularly suitable for the treatment of fruit-beating trees or of vines is a process in which a defined mount of the formulations according to the invention is applied to the stem of the plants with the aid of dosing dispensers, pipettes or syringes, it also being possible for the application devices to be provided with a brushing device or with a surface nozzle to distribute the compositions over a substantial area to cover it entirely. It is also possible to spread the formulations according to the invention onto a solid carrier where they are allowed to harden, to cut up the resulting solid coatings and to attach the individual pieces at the sites where they are desired in each case.

The amounts in which the compositions according to the invention are applied can be varied within a substantial range. They are generally on the order of magnitude which is conventionally chosen for the application of "attract-and-kill formulations".

Preparation and use of the compositions according to the invention is illustrated by the examples which follow.

PREPARATION EXAMPLES.

Example 1

5 g of cyfluthrin and 0.164 g of E,E-8,10-dodecanedienol are dissolved in 94.84 g of the liquid benzotriazole of the formula $$\text{(I-2)}$$

(benzotriazole-N-linked to a phenyl ring bearing $R^3$, OH, and $C_{12}H_{25}$ substituents)

$R^3$=CH$_3$ or C$_2$-C$_{12}$-alkyl with stirring at room temperature. This premix is emulsified in a solution of 2.5 g of ethoxylated nonylphenol with a mean degree of ethoxylation of 10 in 97.5 g of demineralized water at room temperature with the aid of a rotor/stator dispersing rod. This emulsion is treated first with 100 g of a 60% by weight dispersion of polyvinyl acetate in water and then with 80 g of a 2% by weight strength solution of a xanthan-based heteropolysaccharide (Kelzan S®) in water at room temperature with stirring. The resulting viscous substance is spread on a polymer support to form a coating of thickness 1 mm and allowed to stand for 16 hours at room temperature. A solid, rubber-like layer is formed which shows a sponge-like porous structure when observed under the microscope.

Example 2

250 g of the emulsion described in Example 1 are treated first with 100 g of a 60% by weight dispersion of polyvinyl acetate and then with 100 g of a 2% by weight strength solution of a xanthan-based heteropolysaccharide (Kelzan S®) in water at room temperature with stirring. This gives a viscous substance. 4 g of this formulation are poured into a Petri dish of diameter 9 cm and distributed uniformly. After drying at room temperature for 16 hours, a solid, rubber-like layer has formed.

Example 3

200 g of the emulsion described in Example 1 are treated first with 100 g of a 60% by weight dispersion of polyvinyl acetate and then with 80 g of a 2% by weight strength solution of a xanthan-based heteropolysaccharide (Kelzan S®) in water at room temperature with stirring. This gives a viscous substance. 4 g of this formulation are poured into a Petri dish of diameter 9 cm and distributed uniformly. After drying at room temperature for 16 hours, a solid, rubber-like layer has formed.

Example 4

150 g of the emulsion described in Example 1 are treated first with 100 g of a 60% by weight dispersion of polyvinyl acetate and then with 60 g of a 2% by weight strength solution of a xanthan-based heteropolysaccharide (Kelzan S®) in water at room temperature with stirring. This gives a viscous substance. 4 g of this formulation are poured into a Petri dish of diameter 9 cm and distributed uniformly. After drying at room temperature for 16 hours, a solid, rubber-like layer has formed.

Example 5

100 g of the emulsion described in Example 1 are treated first with 100 g of a 60% by weight dispersion of polyvinyl acetate and then with 50 g of a 2% by weight strength solution of a xanthan-based heteropolysaccharide (Kelzan S®) in water at room temperature with stirring. This gives a viscous substance. 4 g of this formulation are poured into a Petri dish of diameter 9 cm and distributed uniformly. After drying at room temperature for 16 hours, a solid, rubber-like layer has formed.

Example 6

5 of β-cyfluthrin are dissolved in 95 g of the liquid benzotriazole of the formula (I-2) (cf. Example 1) with stirring at room temperature. This premix is emulsified at room temperature in a solution of 2.5 g ethoxylated nonylphenol with a mean degree of ethoxylation of 10 in 97.5 g of demineralized water with the aid of a rotor/stator dispersing rod. This emulsion is treated first with 100 g of a 60% by weight dispersion of polyvinyl acetate in water and then with 80 g of a 2% by weight strength solution of a xanthan-based heteropolysaccharide (Kelzan S®) in water at room temperature with stirring. This gives a viscous substance. 4 g of this formulation are poured into a Petri dish of diameter 9 cm and distributed uniformly. After drying at room temperature for 16 hours, a solid, rubber-like layer has formed.

Example 7

5 g of cyfluthrin and 0.041 g of E,E-8,10-dodecanedienol are dissolved in 94.96 g of the liquid benzotriazole (I-2) (cf. Example 1) at room temperature with stirring. This premix is emulsified at room temperature in a solution of 2.5 g of ethoxylated nonylphenol with a mean degree of ethoxylation of 10 in 97.5 g of demineralized water with the aid of a rotor/stator dispersing rod. This emulsion is treated first with 100 g of a 60% by weight dispersion of polyvinyl acetate in water and then with 80 g of a 2% by weight strength solution of a xanthan-based heteropolysaccharide (Kelzan S®) in water at room temperature with stirring. This gives a viscous substance.

Example 8

5 g of cyfluthrin and 0.0041 g of E,E-8,10-dodecanedienol are dissolved in 95.00 g of the liquid benzotriazole (I-2) (cf. Example 1) at room temperature with stirring. This premix is emulsified at room temperature in a solution of 2.5 g of ethoxylated nonylphenol with a mean degree of ethoxylation of 10 in 97.5 g of demineralized water with the aid of a rotor/stator dispersing rod. This emulsion is treated first with 100 g of a 60% by weight dispersion of polyvinyl acetate in water and then with 80 g of a 2% by weight strength solution of a xanthan-based heteropolysaccharide (Kelzan S®) in water at room temperature with stirring. This gives a viscous substance.

Comparison Example 1

(EP-A (European Published Specification) 0 376 888))

A viscous substance is prepared by intimately mixing 3.65 g of cyfluthrin, 0.1 g of E,E-8, 10-dodecanedienol, 70.0 g of the liquid benzotriazole of the formula (I-2) (cf. Example 1), 2.75 g of Aerosil COK 84 (finely divided $SiO_2/Al_2O_3$ powder; 84:16% by weight), 3.52 g of pigment-grade colour black powder Special Black S (density 1.8 to 1.9 g/cm³; particle size 20 nm, surface area 240 m²/g) and 2.71 g of Sudan Black R at room temperature. 4 g of this formulation are poured into a Petri dish of diameter 9 cm and distributed uniformly. After standing at room temperature for several days the formulation was still viscous.

Comparison Example 2

A formulation is prepared as described in Comparison Example 1 which, however, comprises 3.65 g of β-cyfluthrin instead of cyfluthrin. Again a viscous substance is obtained. 4 g of this formulation are poured into a Petri dish of diameter 9 cm and distributed uniformly. After standing at room temperature for several days the formulation still had viscous consistency.

Comparison Example 3

5 g of pulverulent β-cyfluthrin are dispersed in 95 g of an 0.2% by weight strength solution of ethoxylated nonylphenol with a mean degree of ethoxylation of 10 in demineralized water at room temperature with the aid of a rotor/stator dispersing rod. This dispersion is treated first with 100 g of a 60% by weight dispersion of polyvinyl acetate in water and then with 75 g of a 2% by weight strength solution of a xanthan-based heteropolysaccharide (Kelzan S®) in water at room temperature with stirring. This gives a viscous substance. 4 g of this formulation are poured into a Petri dish of diameter 9 cm and distributed uniformly. After drying at room temperature for 16 hours, a solid, rubber-like layer has formed.

Comparison Example 4

10 g of an aqueous suspension concentrate which comprises 5 g of finely-ground β-cyfluthrin are dispersed in 90 g of an 0.2% by weight strength solution of ethoxylated nonylphenol with a mean degree of ethoxylation of 10 in demineralized water at room temperature with the aid of a rotor/stator dispersing rod. This dispersion is treated first with 100 g of a 60% by weight dispersion of polyvinyl acetate in water and then with 75 g of a 2% by weight strength solution of a xanthan-based heteropolysaccharide (Kelzan S®) in water at room temperature with stirring. This gives a viscous substance. 4 g of this formulation are poured into a Petri dish of diameter 9 cm and distributed uniformly. After drying at room temperature for 16 hours, a solid, rubber-like layer has formed.

Comparison Example 5

5 g of cyfluthrin are dissolved in 95.00 g of the liquid benzotriazole (I-2) (cf. Example 1) with stirring at room temperature. This premix is emulsified at room temperature in a solution of 2.5 g of ethoxylated nonylphenol with a mean degree of ethoxylation of 10 in 97.5 g of demineralized water with the aid of a rotor/stator dispersing rod. This emulsion is treated first with 100 g of a 60% by weight dispersion of polyvinyl acetate in water and then with 80 g of a 2% by weight strength solution of a xanthan-based heteropolysaccharide (Kelzan S®) in water at room temperature with stirring. This gives a viscous substance.

Comparison Example 6

A viscous substance is prepared by intimately mixing 3.65 g of cyfluthrin, 70.0 g of the liquid benzotriazole of the formula (I-2) (cf. Example 1), 2.75 g of Aerosil COK 84 (finely divided $SiO_2/Al_2O_3$ powder; 84:16% by weight), 3.52 g of pigment-grade colour black powder Special Blacks (density 1.8 to 1.9 g/cm³; particle size 20 nm, surface area 240 m²/g) and 2.71 g of Sudan Black R at room temperature.

USE EXAMPLES

Example A

To test for insecticidal activity, batches of 10 male codling moths (Cydia Pomonella) are placed on Petri dishes of diameter 9 cm into which 4 g of the formulation in question had been placed in each case 16 hours earlier. After a contact period of 10 minutes, the moths are removed. The morbidity of the moths is subsequently determined as a function of time. In the morbid state, the moths lie motionless on the ground, and uncoordinated twitching of the limbs, the antennae and the abdomen is observed. To assess the insecticidal action quantitatively, the morbidity is plotted in the form of a graph as a function of time. Interpolation allows the period of time to be determined within which 50% of the moths show symptoms of morbidity. This period of time is determined in minutes and designated $t_{50}$. It is used as a measure for the insecticidal activity of the preparation in question. The shorter the $t_{50}$ value, the more efficient the formulation.

The test results can be seen from the table which follows.

TABLE A

| Cydia Pomonella/Insecticidal activity | |
|---|---|
| Preparation | $t_{50}$ (minutes) |
| Examples according to the invention: | |
| 2 | 17 |
| 3 | 20 |
| 4 | 23 |
| 5 | 21 |
| 6 | 17 |
| Comparison examples | |
| 1 | 15 |
| 2 | 37 |
| 3 | 240 |
| 4 | 78 |

Example B

To test for insecticidal activity, batches of 10 male tobacco budworm (Heliothis Virescens) are placed on Petri dishes of diameter 9 cm into which 4 g of the formulation in question had been placed in each case 16 hours earlier. After a contact period of 10 minutes, the moths are removed. The morbidity of the moths is subsequently determined as a function of time. In the morbid state, the moths lie motionless on the ground, and uncoordinated twitching of the limbs, the antennae and the abdomen is observed. To assess the insecticidal action quantitatively, the morbidity is plotted in the form of a graph as a function of time. Interpolation allows the period of time to be determined within which 50

% of the moths show symptoms of morbidity. This period of time is determined in minutes and designated $t_{50}$. It is used as a measure for the insecticidal activity of the preparation in question. The shorter the $t_{50}$ value, the more efficient the formulation.

The test results can be seen from the table which follows.

TABLE B

| Heliothis Virescens/Insecticidal activity | |
|---|---|
| Preparation | $t_{50}$ (minutes) |
| Examples according to the invention: | |
| 6 | 36[1] |
| Comparison examples | |
| 2 | 42[1] |
| 3 | —[2] |
| 4 | —[2] |

[1] After 24 hours, all test insects were dead or showed symptoms of morbidity.
[2] A $t_{50}$ value was impossible to determine. After 24 hours, 90% of the test insects showed no symptoms of poisoning whatsoever.

Example C

To assess the contamination potential of attract-and-kill formulations, a) in each case 0.5 g of the formulation described in Example 1 or b) in each case 0.15 g of the formulation described in Comparison Example 1 are applied to a sheet of glass and distributed uniformly over an area of approximately 10 cm². In both cases, this corresponds to an amount of UV absorber of the formula (I-2) (cf. Example 1) of 125 rag. The sheets are allowed to dry for 24 hours, and the preparations are then covered with in each case one piece of fabric and a pressure is applied for 30 seconds using an area-coveting weight of 1 kg. The contaminated pieces of fabric are subsequently extracted four times using in each case 25 ml of N-methylpyrrolidone. The UV absorber content in the collected extracts is determined spectrophotometrically and calculated as a percentage of the total amount of UV absorber in the preparation.

The amount of UV absorber on the fabric is 4.5 % in the case of the formulation of Example 1 and 73 % in the case of the formulation of Comparison Example 1.

This means that the contamination potential of the formulation in accordance with Comparison Example 1 exceeds the contamination potential of the formulation in accordance with Example 1 by a factor of over 16.

Example D

Determination of the attractant action of attract-and-kill formulations

Air was passed through a wind tunnel of length 1.5 m and a square cross-section of side 0.4 m long at a speed of 0.4 m/s. At the beginning of the tunnel (air inlet side), two cardboard cups were inserted symmetrically into the wind tunnel with the bottom pointing against the direction of flow. The bottom of the cups had been removed with the exception of a narrow web in the middle to allow air to flow through the cups with virtually no hindrance. The inside of the cups was painted with insect glue. A drop (20 rag) of the test formulation was applied to the center of the remaining web of one cup. The other cup was treated with a similar formulation which, however, lacked pheromone (Comparison Example 5 or 6). Batches of 20 male codling moths (Cydia pomonella) 2 days old were released at the end of the tunnel. After 23 hours, the number of the animals trapped in the individual cups was determined and expressed in % as a measure for the attractant action (trapping rate). The results can be seen from the table which follows.

TABLE D

| Attractant action of attract-and-kill formulations | | |
|---|---|---|
| Preparation | Trapping rate with pheromone (%) | Trapping rate without pheromone (%) |
| Examples according to the invention | | |
| 7 | 51 | 12* |
| 8 | 82 | 5* |
| Comparison Example | | |
| 1 | 51 | 20** |

*Comparison Example 5
**Comparison Example 6

Example E

Determination of the attractant action of attract-and-kill formulations

In each case one small apple tree of a mean size of 30 cm was provided in three places (stem, upper side of a leaf and under side of a leaf) with a drop of approximately 50 microliters of the test formulation. Besides the pheromone-comprising formulations according to Example 7 and Comparison Example 1, the pheromone-free comparison formulation according to Example 5 was also tested. In a control experiment, no formulation was applied.

The individual trees together with batches of 15 codling moth (Cydia pomonella) pupae were transferred to gauze cages. In the course of a few days, adults developed from the pupae. The cages were positioned in a wind tunnel (dimensions 3×1.5×1 m). In the course of the eight-day experiment, air was passed through the wind tunnel at a speed of 0.1 m/s. At the end of the experiment, the number of dead insects in the individual cages was determined as a measure for the attract-and-kill action of the formulations and expressed in % as a measure for the mortality. The test results can be seen from the table which follows.

TABLE E

| Attractant action of attract-and-kill formulations | |
|---|---|
| Preparation | Mortality (%) |
| Control — | 12 |
| Example according to the invention 7 | 79 |
| Comparison Examples | |
| 1 | 58 |

TABLE E-continued

| Attractant action of attract-and-kill formulations | |
|---|---|
| Preparation | Mortality (%) |
| Control — | 12 |
| 5 | 25 |

It will be understood that the specification and examples are illustrative but not limitative of the present invention and that other embodiments within the spirit and scope of the invention will suggest themselves to those skilled in the art.

What is claimed is:

1. An insecticidal attract -and-kill formulation comprising 0.1 to 10% by weight of an insecticidally active compound selected from cyfluthrin, β-cyfluthrin and transfluthrin, 0.01 to 1% by weight of a signal substance selected from E,E-8,10-dodecanedienol and Z-11-tetradecenyl acetate, 10 to 90% by weight of a polyvinyl acetate, 10 to 80% by weight of a UV absorber selected from a benzotriazole of the formula

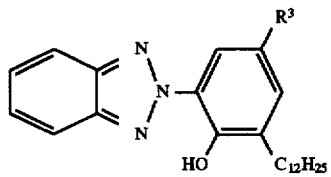

in which

R³ represents methyl or $C_2$–$C_{12}$-alkyl, a 2-hydroxy-4-methoxy-benzophenone of the formula

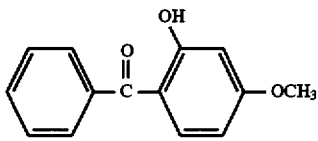

and 2-(2-ethyl-hexyl)-2-cyano 3,3-diphenyl-2-propenoate of the formula

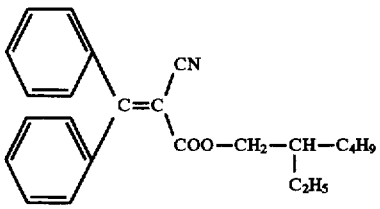

0.1 to 4% by weight of a surfactant, and water which, after drying the aqueous emulsion formed above, forms a sponge-like mass or a porus film.

2. A method for combating harmful insects and undesirable representatives of the order Acarina in agriculture, forestry and in horticulture, which method comprises applying to the plants to be protected or to their habitat an effective amount of a composition according to claim 1.

* * * * *